United States Patent [19]

Frank

[11] Patent Number: 4,946,973

[45] Date of Patent: Aug. 7, 1990

[54] STEREOSELECTIVE EPOXIDATION OF CYCLIC 4-HYDROXY OLEFINS

[75] Inventor: Walter C. Frank, Holland, Pa.

[73] Assignee: Union Camp Corporation, Princeton, N.J.

[21] Appl. No.: 247,057

[22] Filed: Sep. 20, 1988

[51] Int. Cl.$^5$ .............................................. C07D 301/14
[52] U.S. Cl. ..................................... 549/525; 549/529; 549/531
[58] Field of Search .......................... 549/529, 531, 525

[56] References Cited

U.S. PATENT DOCUMENTS 3,053,856  9/1962  Payne et al. ........................ 549/525

FOREIGN PATENT DOCUMENTS 114979  5/1987  Japan .

OTHER PUBLICATIONS

R. G. Carlson, et al., *J. Org. Chem.*, "Epoxidation," 36, pp. 3832–3833, (1971).
C. H. Gragnieu, et al., *J. Chem. Soc. Perkin I*, "A New Procedure for Olefin Oxiranation by Peroxybenzimidic Acid" . . . , pp. 1009–1011, (1982).
F. A. Corey and R. J. Sundberg, "Advanced Organic Chemistry," 2nd ed., pp. 494–498, Plenum Press, New York (1983).
*Chemical Abstracts* 107: 154227a, Abstract of Japanese Patent 62-114,979.
Achmatowicz and Szechner, *Carbohydrate Res.*, 50, pp. 23–33, (1976).

*Primary Examiner*—Richard L. Raymond
*Assistant Examiner*—Mark W. Russell
*Attorney, Agent, or Firm*—Edward J. Sites

[57] ABSTRACT

The stereoselective expoxidation of cyclic 4-hydroxy olefins is disclosed. These methods involve contacting the cyclic 4-hydroxy olefin with peroxycarboximidic acid, which is preferably generated in situ by contacting an organic nitrile with aqueous hydrogen peroxide. The invention provides unexpectedly high yields of the corresponding cis-epoxides.

37 Claims, No Drawings

STEREOSELECTIVE EPOXIDATION OF CYCLIC 4-HYDROXY OLEFINS

BACKGROUND OF THE INVENTION

This invention relates to the stereoselective epoxidation of cyclic 4-hydroxy olefins and, more specifically, to the stereoselective epoxidation of terpinen-4-ol.

Epoxidation is the conversion of olefins (or other substances containing carbon-carbon double bonds) into epoxy (oxirane) compounds. An epoxidation is considered stereoselective when its epoxide product comprises a substantial percentage of a single one of its possible isomeric products.

Base catalyzed epoxidation of olefins has been described previously by Payne in U.S. Pat. No. 3,053,856, in which organic nitrile compounds and hydrogen peroxide were employed to generate the active epoxidizing agent peroxycarboximidic acid in situ. However, only moderate product yields were obtained. Solvent concentrations of greater than 50% by weight were necessary, and concentrations greater than 70% were preferred. This necessity for high solvent concentrations gave rise to poor reactor efficiencies. Subsequent to publication of the patent, Carlson (*J. Org. Chem.*, 36, 3832-33, 1971) taught that a peroxycarboximidic acid generated in situ by methods such as that disclosed by Payne is a less selective and more reactive epoxidizing agent than a chemically-similar peroxycarboxylic acid fully synthesized apart from the epoxidation reaction sequence then added thereto. When peracetic acid is allowed to react with terpinen-4-ol an approximate three to one mixture of the cis: trans epoxies is obtained which is undesirable because of the large amounts of the trans isomer present in the final product.

More recently, Achmatowicz and Szechner (*Carbohydrate Res.*, 50, 23-33, 1976) described a stereoselective epoxidation of unsaturated carbohydrates using a peroxycarboximidic acid. Again, yields were moderate. Excellent stereoselectivity was achieved only when three oxygen substituents on the same face of the molecule could hydrogen bond to the peroxycarboximidic acid, thereby preferentially directing the acid's attack on the carbon-carbon double bond from that face of the molecule. For isomeric carbohydrates having one stereochemically inverted center bearing an oxygen-containing substituent, a much lower stereoselectivity of epoxidation was observed. In addition, high solvent concentrations were required.

Gagnieu and Grouiller (*J. Chem. Soc. Perkin Trans. I*, 1009-11, 1982) reported similar results with other unsaturated carbohydrates. Only where three oxygen substituents were on the same side of the molecule could high stereoselective epoxidation be accomplished. Systems with two oxygen substituents gave much lower epoxidation stereoselectivity. Again, highly solvent-diluted systems were necessary to perform the reaction.

In European Patent Application No. 151,941 McElligott described the phase transfer epoxidation of terpinen-4-ol to obtain the corresponding cis epoxide product in yields of about 75%; the epoxidizing agents employed were peroxo metal catalysts used in conjunction with stoichiometric amounts of oxidant ($H_2O_2$) under phase transfer conditions. A compromise between conversion and selectivity, highest selectivity being at lower conversions, and vice versa was shown.

Therefore, it is an object of this invention to stereoselectively epoxidize cyclic 4-hydroxy olefins. It is a further object of this invention to stereoselectively epoxidize terpinen-4-ol to cis-1,2-epoxyterpinen-4-ol. It is another object of this invention to effect such epoxidation without the employment of phase transfer reagents. It is still another object of this invention to effect such epoxidation with peroxycarboximidic acid. It is yet another object of this invention to effect such epoxidation with peroxycarboximidic acid which is generated in situ. It is a particular object of this invention to do so in a more commercially practical manner than possible employing previously-known techniques.

SUMMARY OF THE INVENTION

In accordance with this invention, it has been found that peroxycarboximidic acid generated in situ by contacting an organic nitrile compound and hydrogen peroxide can be advantageously employed in the steroselective epoxidation of cyclic 4-hydroxy olefins to their corresponding cis-epoxides when the reaction mixture is maintained at a pH greater than about 6. The invention provides such cis-epoxides in unexpectedly high yields. The invention minimizes the use of solvent, thereby increasing reactor efficiency.

It has been found that terpinen-4-ol can be epoxidized with a peroxycarboximidic acid to yield a cis/trans ratio of over 40:1 and up to about 75:1. This unexpected result is highly beneficial.

The cyclic 4-hydroxy olefins of this invention have formula:

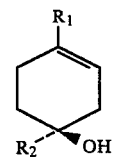

and yield preferentially:

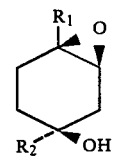

where $R_1$ and $R_2$ are the same or different and are hydrogen or hydrocarbyl having from 1 to about 6 carbon atoms. It is particularly preferred that the cyclic 4-hydroxy olefin be terpinen-4-ol ($R_1$=—$CH_3$, $R_2$=—$CH(CH_3)_2$).

In preferred embodiments of the invention, terpinen-4-ol is provided in solution form; solutions of terpinen-4-ol in an inert organic solvent are particularly preferred. An inert organic solvent does not enter into or otherwise adversely affect the desired course of the epoxidation reaction; a representative and preferred inert organic solvent is methanol. In the practice of this invention, the solvent preferably comprises less than about 50 weight percent of the total reaction mixture; it is especially preferred that solvent comprise between about 10 and about 30 weight percent.

The peroxycarboximidic acid epoxidizing agent is preferably formed using an aqueous solution of hydrogen peroxide. The concentration of the hydrogen peroxide solution is not believed to be a critical factor.

However, it is preferred that the hydrogen peroxide solution have a concentration of between about 2 and 50 weight percent.

In a preferred embodiment, the epoxidation is initiated by bringing the terpinen-4-ol, the hydrogen peroxide solution and the nitrile together in a suitable reaction vessel. The nitrile is believed to react first with the hydrogen peroxide at neutral to alkaline pH to form a peroxycarboximidic acid. Nitriles amenable to the practice of this invention include benzonitrile, ethanenitrile or acetonitrile, 3-cyanopyridine, and 2-cyanopyridine. Compounds having a plurality of cyano junctions may also be used, such as 1,4-dicyanobutane. As will be appreciated by one of skill in the art, a wide variety of nitriles may advantageously be so employed.

In the practice of this invention, it is believed important that the terpinen-4-ol epoxidation reaction mixture be maintained at a pH value greater than 6; the range from about 8 to about 11 is preferred. The desired pH can be obtained by the addition of appropriate proportions of basic compounds. Any inorganic salts or bases which maintain the pH in the desired region should be effective. Representative basic compounds which may be advantageously so employed are ammonium carbonate, ammonium bicarbonate, calcium carbonate, potassium carbonate, potassium bicarbonate, sodium bicarbonate, lithium hydroxide monohydrate, sodium hydroxide, and magnesium hydroxide. Organic bases such as amines may also be employed, except for such bases as may interfere with the desired reactions. Tertiary amines are likely useful for this function. When 3-cyanopyridine or 2-cyanopyridine are used as the nitrile reactant, usually no additional basic compound should be required.

The method of the invention may be carried out over a wide range of temperatures, preferably from about room temperature to 75° C. A wide range of pressure conditions may also be employed; it is preferred that this invention be practiced at atmospheric pressure (1.0 atmosphere).

A number of the chemical compounds employed in the practice of this invention exist in different isomeric forms. Certain pairs of such isomers are non-superimposable mirror images of one another. These pairs are called enantiomers or optical isomers; each member of such a pair is, by definition, chiral asymmetric). Optical isomers differ from each other in two principal respects: they react with other chiral molecules at different rates, and solutions comprised of single optical isomers rotate plane-polarized light in different directions. On the basis of such rotation, one optical isomer is designated the dextrorotator enantiomer and one optical isomer is designated the levorotatory enantiomer. For example, terpinen-4-ol has two such optical isomers. When a chemical compound is comprised of more of one optical isomer than the other, it is said to be optically enriched or, alternatively, optically active.

Interestingly, when an optically enriched form of terpinen-4-ol is employed in the practice of this invention, this optical activity —which is transmitted directly to the resulting epoxy product —is not appreciably reduced or destroyed. In addition, the use of optically active nitriles in epoxidizing optically inactive terpinen-4-ol provides an optically enriched product. The optical rotation thus enriched depends upon the particular nitrile chosen, as would be appreciated by one skilled in the art.

The method of the invention may also be carried out in the presence of agents such as 8-hydroxyquinoline, added in an amount effective to stabilize the reaction mixture; for example, against peroxide decomposition by free radicals.

In preferred embodiments of this invention, the molar ratio of nitrile to hydrogen peroxide is between about 0.8:1.0 and 3.0:1.0. The preferred molar ratio of terpinen-4-ol to hydrogen peroxide is between about 2.0:1.0 and 1.0:3.0; it is especially preferred that said ratio be between 1.0:0.9 and 1.0:1.25.

The invention is further described in connection with the following examples thereof wherein parts and percents are by weight unless otherwise specified.

EXAMPLE 1

To 10 milliliters of methanol is added 11.29 grams of 97% pure terpinen-4-ol, 5.5 grams of acetonitrile and 1.3 grams of potassium bicarbonate. The mixture is heated to 60°-65° C. At this temperature, hydrogen peroxide (7.9 milliliters of a 30% aqueous solution) is added at a rate of 0.15 milliliters/minute. Fifteen minutes after the addition is complete, the mixture is cooled. The methanol solvent and the acetonitrile are then evaporated. The residue is dissolved in dichloromethane and washed with a brine solution. The organic components are separated, dried with $Na_2SO_4$, filtered, and evaporated. A 12.23 gram product was analyzed and found to contain 95.44 wt.% cis-1, 2-epoxyterpinen-4-ol by internal standard G.C. analysis. The molar yield is 96.5%. The cis:trans epoxide ratio was greater than 90:1.

EXAMPLE 2

A 4-necked, round bottom flask fitted with a stirrer, condenser, thermocouple and two addition funnels was charged with 10 milliliters of methanol, 1.28 grams of potassium bicarbonate and 5.5 grams of acetonitrile. The mixture was then heated to 65° C. Terpinen-4-ol (11.29 grams, 92.3% pure) and hydrogen peroxide (7.9 milliliters of a 34.4% aqueous solution) were added independently and simultaneously over one hour via the additional funnels. The temperature was maintained at 65-70° C. during the addition. After 0.5 hours additional stirring at 65° C., the reaction mixture was tested for peroxide using starch indicator paper. Upon a negative test the solvent portion thereof was evaporated. The resulting residue was dissolved in methylene chloride (100 milliliters), washed with brine, and dried over anhydrous $Na_2SO_4$ to yield 11.33 grams of a crude product which contained 74.8% cis-1,2-epoxyterpinen-4-ol and 16.0% terpinen-4-ol. The cis:trans epoxide ratio was greater than 78:1. The yield corresponds to 82.6% conversion and 89.2% selectively as analyzed by gas chromatography using an internal standard.

EXAMPLE 3

Methanol (2.5 milliliters), terpinen-4-ol (11.28 grams, 92.3% pure), acetonitrile (5.50 grams) and potassium bicarbonate (1.28 grams) were added with stirring to a 3-necked round bottom flask equipped with thermocouple, condenser, and addition funnel. The mixture was heated to 65° C. and 7.9 milliliters of a 32.4% aqueous hydrogen peroxide solution was added over a one hour period. The temperature was maintained at 65-70° C. during the addition. After an additional 0.5 hour at 65° C. and a negative test for peroxide, the reaction mixture was solvent stripped. The residue was dissolved in methylene chloride (100 milliliters), washed with brine, and dried over anhydrous Na₂SO₄ to yield 11.18 grams of crude product which contained 47.1% cis-1,2-epoxyterpinen-4-ol and 43.4% terpinen-4-ol. The cis:-trans epoxide ration was greater than 40.7:1. The yield corresponded to 53.4% conversion and 90.6% selectivity, based on analysis of isolated product by gas chromatography with an internal standard.

EXAMPLE 4

A 4-necked, round bottom flask fitted with a stirrer, a thermocouple, a Claisen adapter, a condenser, and 3 addition funnels was charged with 10 milliliters of methanol and 1.28 grams of potassium bicarbonate. The mixture was heated to a temperature of 65° C. Terpinen-4-ol (11.29 grams, 92.3% pure), 32.4% aqueous hydrogen peroxide (7.9 milliliters), and acetonitrile (5.5 grams) were added independently and simultaneously over a 1.5 hour period via the addition funnels. The temperature was maintained at 65°-70° C. during the addition. After an additional reaction time of 0.5 hour at 65° C. and a negative peroxide test by indicator paper, the reaction mixture was solvent stripped. The residue was dissolved in methylene chloride (100 milliliters), washed with brine, and dried over anhydrous Nahd 2SO₄ to yield 12.00 grams of crude product which contained 87.6% cis-1,2-epoxy-terpinen-4-ol and 2.3% terpinen-4-ol. The cis:trans epoxide ratio was greater than 74:1. The yield corresponds to 97.4% conversion and 93.8% selectivity by gas chromatography with an internal standard.

EXAMPLE 5

A 3-necked, round bottom flask fitted with a stirrer, thermocouple, a condenser, and an addition funnel is charged with 5 milliliters of methanol, 11.30 grams of terpinen-4-ol (92.3% pure) and 1.28 gram of potassium bicarbonate.

The mixture was heated to 67° C. A solution of 32.4% aqueous hydrogen peroxide (7.9 milliliters), acetonitrile (5.5 grams) and methanol (5 milliliters) was added over a 1.5 hour period maintaining the reaction temperature at 65°-70° C. After an additional reaction time of 0.5 hour at 65° C., the reaction mixture was worked up as described in Example 4. The yield of crude product was 11.13 grams, which contained 58.6% terpinen-4-ol and 30.9% cis-1, 2-epoxy-terpinen-4-ol. The cis:trans epoxide ratio was greater than 63:1. The yield corresponds to 37.5% conversion and 79.6% selectivity by gas chromatography with an internal standard.

EXAMPLE 6

Methanol (10 milliliters), terpinen-4-ol (11.29 grams, 92.3% pure) ammonium carbonate (1.28 grams) and acetonitrile (5.5 grams) were added to a 3-necked round bottom flask equipped with condenser, stirrer, addition funnel, and thermocouple. The mixture was heated to 30° C. and 32.4% aqueous hydrogen peroxide (7.9 milliliters) was added. The mixture was then heated to 65° C. for 0.5 hours. The mixture tested negative for peroxides at this time and was worked up as described in Example 4. The yield of crude product was 11.53 gram and contained 23.1% terpinen-4-ol and 66.4% cis-1,2-epoxyterpinen-4-ol. This corresponds to a 74.5% conversion to the cis epoxide with 89.4% selectivity, based on a gas chromatography analysis with an internal standard. The cis:trans epoxide ratio was greater than 24.5:1.

What is claimed is:

1. A method for the stereoselective synthesis of a cyclic epoxy alcohol having formula:

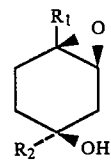

wherein $R_1$ and $R_2$ are the same or different and are hydrogen or hydrocarbyl having from 1 to about 6 carbon atoms, said method comprising:
contacting a cyclic hydroxy olefin having formula:

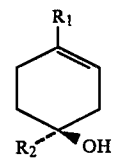

with peroxycarboximidic acid;
in a reaction mixture maintained at a pH greater than about 6 comprising an organic solvent inert with respect to the conditions of contacting;
for a period of time effective to result in cis-epoxidation of said hydroxy olefin.

2. The method of claim 1 wherein peroxy-carboximidic acid is generated in situ.

3. The method of claim 1 wherein peroxycarboximidic acid is generated in situ by contacting hydrogen peroxide and a nitrile having formula $R_3$—CN, where $R_3$ is hydrocarbyl or heterocyclic having from about 1 to about 7 carbon atoms.

4. The method of claim 3 wherein the nitrile is 2-cyanopyridine.

5. The method of claim 3 wherein the nitrile is 3-cyanopyridine.

6. The method of claim 3 wherein the nitrile has a plurality of cyano functions.

7. The method of claim 3 wherein the nitrile is optically enriched in its dextrorotatory enantiomer.

8. The method of claim 3 wherein the nitrile is optically enriched in its levorotatory enantiomer.

9. The method of claim 1 wherein the inert solvent is methanol.

10. The method of claim 1 wherein the inert organic solvent comprises less than about 50 weight percent of said reaction mixture.

11. The method of claim 1 wherein the inert organic solvent comprises between about 10 and about 30 weight percent of said reaction mixture.

12. The method of claim 1 wherein the pH of the reaction mixture is maintained between about 8 and 11.

13. The method of claim 1 wherein the pH is maintained by addition of composition comprising at least one base selected from the group consisting of ammonium carbonate, ammonium bicarbonate, calcium carbonate, potassium carbonate, potassium bicarbonate, sodium bicarbonate, lithium hydroxide monohydrate, sodium hydroxide, and magnesium hydroxide.

14. The method of claim 1 where pH is maintained by the addition of an organic base.

15. The method of claim 1 wherein the temperature of the reaction mixture is maintained at about 75° C. corrected for pressure.

16. The method of claim 1 wherein the cyclic 4-hydroxy olefin is optically enriched in its dextrorotatory enantiomer.

17. The method of claim 1 wherein the cyclic 4-hydroxy olefin is optically enriched in its levorotatory enantiomer.

18. The method of claim 1 wherein the hydrogen peroxide is stabilized by addition of a stabilizing agent.

19. The method of claim 18 wherein the stabilizing agent is 8-hydroxyquinoline.

20. A method for the stereoselective synthesis of cis-1,2-epoxyterpinen-4-ol comprising:
   contacting terpinen-4-ol with peroxycarboximidic acid;
   in a reaction mixture maintained at a pH greater than about 6, comprising an organic solvent inert with respect to the conditions of contacting;
   for a period of time effective to result in substantial cis-epoxidation of terpinen-4-ol.

21. The method of claim 20 wherein peroxycarboximidic acid is generated in situ.

22. The method of claim 20 wherein peroxycarboximidic acid is generated in situ by contacting hydrogen peroxide and a nitrile having formula $R_3$—CN, where $R_3$ is hydrocarbyl or heterocyclic having from about 1 to about 7 carbon atoms.

23. The method of claim 22 wherein the nitrile is 2-cyanopyridine.

24. The method of claim 22 wherein the nitrile is 3-cyanopyridine.

25. The method of claim 22 wherein the nitrile is optically enriched in its dextrorotatory enantiomer.

26. The method of claim 22 wherein the organic nitrile compound is optically enriched in its levorotatory enantiomer.

27. The method of claim 20 wherein the inert solvent is methanol.

28. The method of claim 20 wherein the inert organic solvent comprises less than about 50 weight percent of said reaction mixture.

29. The method of claim 20 wherein the inert organic solvent comprises between about 10 and about 30 weight percent of said reaction mixture.

30. The method of claim 20 wherein the pH of the reaction mixture is maintained between about 8 and 11.

31. The method of claim 20 wherein the pH is maintained by addition of composition comprising at least one base selected from the group consisting of ammonium carbonate, ammonium bicarbonate, calcium carbonate, potassium carbonate, potassium bicarbonate, sodium bicarbonate, lithium hydroxide monohydrate, sodium hydroxide, and magnesium hydroxide.

32. The method according to claim 20 wherein the pH is maintained by the addition of an organic base.

33. The method of claim 20 wherein the temperature of the reaction mixture is maintained at about 75° C., corrected for pressure.

34. The method of claim 20 wherein the terpinen-4-ol is optically enriched in its dextrorotatory enantiomer.

35. The method of claim 20 wherein the terpinen-4-ol is optically enriched in its levorotatory enantiomer.

36. The method of claim 20 wherein the hydrogen peroxide is stabilized by addition of a stabilizing agent.

37. The method of claim 36 wherein the stabilizing agent is 8-hydroxyquinoline.

* * * * *